United States Patent [19]

Cohen et al.

[11] 4,434,101

[45] Feb. 28, 1984

[54] INHIBITORS OF SRS-SYNTHESIS

[75] Inventors: Noal Cohen, Montclair; Giuseppe Weber, Cedar Grove, both of N.J.

[73] Assignee: Hoffmann-La Roche Inc., Nutley, N.J.

[21] Appl. No.: 301,614

[22] Filed: Sep. 14, 1981

[51] Int. Cl.$^3$ .......................... C11C 3/02; A61K 31/23
[52] U.S. Cl. ............................. 260/410.9 R; 260/413; 560/205; 560/210; 562/598; 549/420; 424/312; 424/318
[58] Field of Search ..................... 260/410.9 M, 413 L

[56] References Cited

U.S. PATENT DOCUMENTS

| | | | |
|---|---|---|---|
| 2,934,570 | 4/1960 | Goldberg et al. | 260/410.9 M X |
| 3,450,821 | 6/1969 | Carstensen et al. | 260/413 L X |
| 3,952,035 | 4/1976 | Galantay et al. | 260/413 L |
| 3,972,907 | 8/1976 | Baran et al. | 260/410.9 M |

OTHER PUBLICATIONS

Heslinga et al., CA 85:93754s (1976).
Fryer et al., CA 82:97629r (1975).
Liang et al., CA 93:25952v (1980).
Yeh et al., Tetrahedron Letters No. 49, pp. 4257–4260 (1977).
Carl D. Perchonock, Tetrahedron Letters, 24, pp. 2457–2460, 1983.

*Primary Examiner*—Thomas A. Waltz
*Attorney, Agent, or Firm*—Jon S. Saxe; George M. Gould; William H. Epstein

[57] ABSTRACT

Methyl derivatives of arachidonic acid and intermediates thereto have been synthesized. These derivatives are inhibitors of SRS-A synthesis and are useful for treating and preventing allergic reactions.

3 Claims, No Drawings

INHIBITORS OF SRS-SYNTHESIS

BACKGROUND OF THE INVENTION

In mammals, essential fatty acids such as arachidonic acid serve as substrates for cellular biological processes producing prostaglandins and the material SRS-A (Slow Reacting Substance of Anaphylaxis), the pathway to prostaglandins being catalyzed by prostaglandin synthetase and the pathway to SRS-A being catalyzed by lipoxygenase. The prostaglandin pathway leads to products of known beneficial function in mammals, while the SRS-A pathway produces products which have no known beneficial function in mammals.

After its cellular biosynthesis SRS-A is released from the cell of origin and produces effects such as bronchoconstriction during an allergic response. There has been an ongoing need for agents that will specifically inhibit the synthesis of SRS-A by mammalian cells in order to prevent the release of SRS-A and the resulting asthmatic conditions thereto. In the past, methyl derivatives of arachidonic acid have been prepared. These derivatives relate to the inhibition of prostaglandin synthesis in order to treat disorders apparently arising therefrom.

In particular arachidonic acids methylated in the 2 or 3 position of the chain have been made by classical procedures wherein the intact arachidonic acid compound is methylated [Liang et al., Adv. Prost. Thrombox. Res. 6, 235 (1980)]. Also arachidonic acid analogs methylated in the 13 position have been disclosed by Yeh and Dawson, Tetrahedron Letters No. 49, pp 4257–4260, (1977). This disclosure relates to compounds which have potential prostaglandin synthetase inhibitory activity.

SUMMARY OF THE INVENTION

In accordance with this invention, compounds are provided which inhibit the synthesis of SRS-A without inhibiting the synthesis of prostaglandins. The compounds of this invention are compounds of the formula

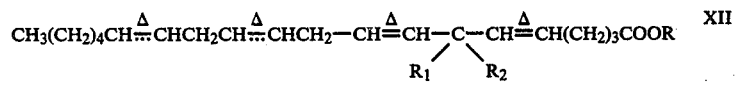

wherein Δ designates cis configuration across a double bond; the dotted lines designate optionally a double bond or a hydrognated bond; R represents hydrogen or lower alkyl; and $R_1$ and $R_2$ represent hydrogen or methyl with the proviso that where one of $R_1$ and $R_2$ is hydrogen the other is methyl; and pharmaceutically acceptable base addition salts thereof when R is hydrogen.

The compounds of formula XII are prepared from novel intermediates of the formula

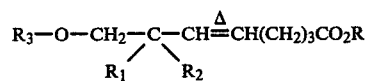

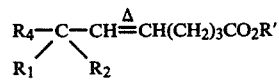

wherein Δ, the dotted lines, R, $R_1$ and $R_2$ are as defined earlier; $R_3$ represents hydrogen or an ether protecting group; $R_4$ represents —CH$_2$OH or —CHO; R' represents lower alkyl and R'' represents a phosphonium salt whereby a compound of formula IV is converted to a compound of formula VI which is treated with a compound of formula X to produce a compound of formula XII.

The compounds of formulas IV, VI, X and XII are produced such that the stereo configuration about a carbon-carbon double bond is cis.

The compounds of formula XII have been discovered to be potent inhibitors of SRS-A synthesis and therefore are useful as anti-allergic agents or anti-asthmatic agents; while compounds of formulas IV, VI and X have been discovered to be useful in producing compounds of formula XII. The compounds of formula XII are specific inhibitors of SRS-A production, but such compounds do not significantly affect the biosynthesis of prostaglandins.

DETAILED DESCRIPTION OF INVENTION

The term "lower alkyl" comprehends both straight and branched chain saturated hydrocarbon groups having 1 to 7 carbon atoms, such as methyl, ethyl, propyl, isopropyl and the like.

The term "phosphonium salt" comprehends any phosphonium salt capable of forming a cis carbon-carbon double bond when such salt is condensed in a Wittig reaction with an aldehyde in the presence of a strong base. Among such phosphonium salts there are especially included the triaryl-phosphonium halides such as triphenyl or tritolylphosphonium halides. The triphenylphosphonium halide is preferred. Strong bases which may be employed in the Wittig reaction include such bases as lower alkyl-or aryllithium reagents such as phenyllithium, methyllithium, n-butyllithium and the like, wherein n-butyllithium is preferred.

The term "halide" comprehends conventionally compounds containing a halogen which is inclusive of such atoms as bromine, chlorine, fluorine and iodine.

The term "ether protecting group" comprehends a hydrolyzable ether group removable by conventional hydrolysis or acid catalyzed cleavage. Any conventional ether group that may be hydrolyzed or cleaved by acid to yield a hydroxy group can be utilized as the ether protecting group. For example ether protecting groups useful for the purpose of this invention include tetrahydropyranyl ethers, ethoxyethylethers, methoxy isopropyl ethers, and aryl or aryl lower alkyl ethers such as benzhydryl, trityl and the like.

Acid catalyzed cleavage of the ether protecting group may be carried out by conventional treatment with a strong organic or inorganic acid. Among the organic acids there are included lower alkanoic acids, i.e. acids having 2 to 7 carbon atoms, such as acetic acid, propionic acid, and the like. Inorganic acids are preferred. Among the preferred inorganic acids are the mineral acids such as sulfuric acid, hydrochloric acid and the like. In carrying out this reaction, temperature and pressure are not critical and this reaction may be carried out at room temperature and atmospheric pressure.

The term "cis" represented by $\Delta$ designates the fact that the two largest groups attached across a carbon-carbon double bond are on the same side of such double bond.

The compounds of formula XII can be used in accordance with this invention in their salt form. Any conventional pharmaceutically acceptable base addition salts of the compounds of formula XII may be utilized. Pharmaceutically acceptable base addition salts include any conventional non-toxic salt such as the sodium salt, potassium salt, ammonium salt and the like, formed by neutralization of the acid form of compounds of formula XII with an alkaline metal hydroxide or ammonium hydroxide.

The processes of the present invention relate to processes by which the cis configuration of the olefinic bonds in compounds of formula XII are formed. These processes are summarized in the following reaction schemes I, II and III. For such reactions, temperature and pressure of the resulting reaction mixture are not critical, unless otherwise noted, and room temperature and atmospheric pressure are suitable for carrying out these reactions, as well as elevated or reduced temperatures and pressures. Where it is noted that a reaction is carried out under an inert atmosphere, any conventional inert gas can be utilized in a conventional manner to create the inert atmosphere. Generally such inert gases include for example argon, nitrogen, or helium. A critical feature of each reaction is such that any resulting carbon-carbon double bond formed in a reaction product occurs in or be maintained in the cis configuration.

wherein $\Delta$, R', $R_1$, $R_2$ and $R_3$ are as defined earlier.

Reaction Scheme II

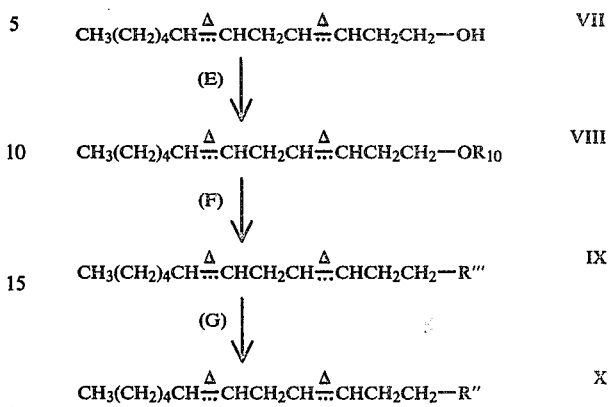

wherein $\Delta$, the dotted lines and R" are as defined earlier; $R_{10}$ represents lower alkyl or aryl sulfonyl; and R'" represents a halide.

Reaction Scheme III

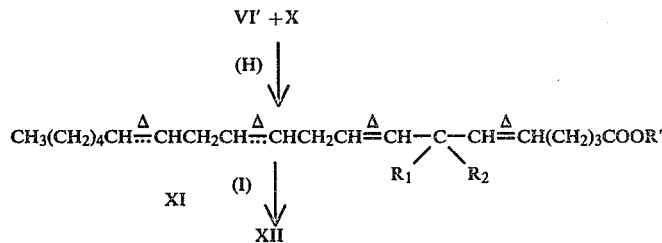

wherein $\Delta$, the dotted lines, $R_1$, $R_2$ and R' are as defined earlier.

Step A

In step A of reaction scheme I, the starting compounds are the compounds of formula I and II which are reacted via a Wittig reaction in a conventional manner to produce the compound of formula III. The weight ratio of compound of formula I to the compound of formula II is not critical but it is preferred that the compound of formula II be in stoichiometric excess Reaction Scheme I

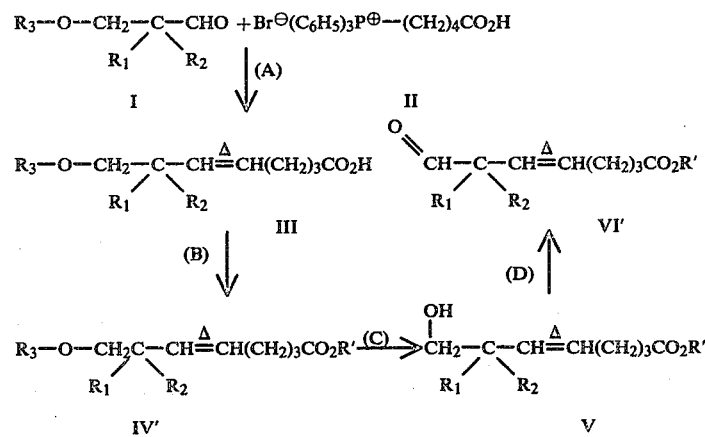

to the compound of formula I. This reaction of step A is a condensation reaction between an aldehyde, e.g. a compound of formula I and a phosphonium halide salt, e.g. the compound of formula II in a cis-stereoselective Wittig reaction. This reaction is generally carried out using a deprotonating agent such as an alkyl or aryl lithium base such as n-butyllithium in an ether solvent such as tetrahydrofuran and a co-solvent of tetramethylethylenediamine or hexamethylphosphorictriamide. Temperature and pressure for this reaction are not critical but it is preferred that the reaction be carried out between −30° C. and room temperature at atmospheric pressure.

It is an essential feature of this reaction step that the resulting carbon-carbon double bond formed in the reaction product, i.e., the compound of formula III, be in the cis configuration. Any of the conventional conditions used for producing such a cis configuration by a Wittig reaction can be used to carry out this step.

More particularly for example a compound of formula I such as the compound of formula

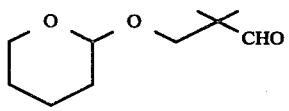   I' may be reacted via Wittig reaction with a compound of formula II to produce a compound of formula III such as the compound of formula

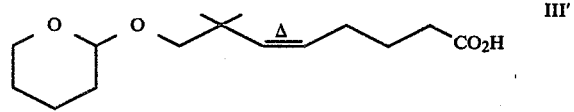   III' wherein $\Delta$ is a described earlier.

Step B

A compound of formula III is converted to a compound of formula IV in Step B of Reaction Scheme I by esterification. The compound of formula III can be esterified by any conventional means using any conventional esterifying agent such as diazomethane or a lower alkyl halide. The cis configuration of the carbon-carbon double bond in the compound of formula III will be maintained in the compound of formula IV' under the conventional conditions for esterification.

More particularly for example a compound of formula III such as the compound of formula III' may be esterified conventionally by the esterifying agent $CH_2N_2$ to provide the compound of formula

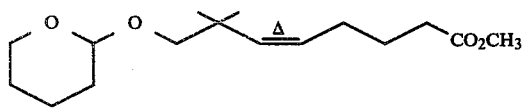   IV''' wherein $\Delta$ is as described earlier.

Step C

A compound of formula IV' is converted to a compound of formula V in Step C of reaction Scheme I by hydrolysis of the ether bond formed by $R_3$ (an ether protecting group) to yield a hydroxy group in the compound of formula V. This hydrolysis reaction may be carried out as described earlier utilizing conventional hydrolysis or an acid catalyzed cleavage reaction of the ether protecting group.

More particularly for example a compound of formula IV' such as the compound of formula IV''' may be hydrolyzed by an acid such as dilute hydrochloric acid to provide by the acid catalyzed cleavage the compound of formula

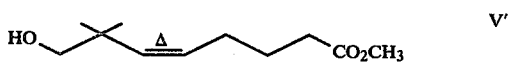   V' wherein $\Delta$ is as described earlier.

Step D

The compound of formula V is converted to the compound of formula VI' in Step D of Reaction Scheme I by treating the compound of formula V with an oxidizing agent. Any conventional oxidizing agent which may be utilized to convert a primary alcohol to an aldehyde can be used. Among the preferred oxidizing agents are included chromium trioxide dipyridine complex, pyridinium dichromate, and the like. Any of the conditions conventionally utilized with these oxidizing agents can be utilized in this conversion.

The compound of formula VI' resulting from the reaction of Step D of Reaction Scheme I is employed in Step H of the reactions of Reaction Scheme III.

More particularly for example a compound of formula V such as the compound of formula V' may be oxidized by treatment with a chromate oxidizing agent to provide the compound of formula

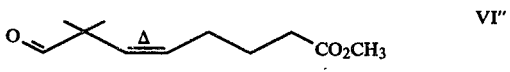   VI'' wherein $\Delta$ is as described earlier.

Step E

In Step E of reaction Scheme II, a compound of formula VII is activated by reacting such compound with a sulfonating agent to provide a compound of formula VIII. Any agent such as a lower alkyl or aryl sulfonyl halide which will react with the hydroxy group of the compound of formula VII to provde another group, i.e. an activated group for introducing a halide, may be used as the sulfonating agent. Among such agents are included for example such compounds as methanesulfonyl chloride, benzenesulfonyl chloride, p-toluenesulfonyl chloride (p-TsCl) and the like. Step E of reaction Scheme II may be by-passed to Step F wherein the compound of formula VII is halogenated conventionally by a halogenating agent to provide the compound of formula IX. For such a by-pass, any of the conventional conditions for halogenating an alcohol via any conventional halogenating agent may be used to carry out a reaction of converting a compound of formula VII to a compound of formula IX. It is preferred, however, that Step E be performed in order to achieve a high yield in the halogenation process.

Step F

A compound of formula VIII is halogenated in Step F to provide a compound of formula IX. The halogenation will replace the activated group of the compound of formula VIII with a halogen from a halogenating agent. The halogenating agent may be a halogen or salt thereof such as for example an alkali metal halide such as NaI, LiI, KI, CsI and the like.

More particularly for example a compound of formula VIII may be reacted with a halogenating agent such as NaI conventionally to provide the compound of formula

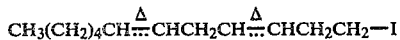   IX' wherein Δ and the dotted lines are as previously described.

Step G

A compound of formula IX is converted to the compound of formula X in Step G by treating the compound of formula IX with a phosphine. Any phosphine which will react with a compound of formula IX to provide a phosphonium halide capable of condensation in a Wittig reaction with a compound of formula VI' to provide thereby the formation of a cis carbon-carbon double bond may be utilized as the phosphine. Among such phosphines are included for example the triarylphosphines such as triphenylphosphine and tritolylphosphine.

More particularly for example a compound of formula IX such as the compound of formula IX' may be reacted with a phosphine such as triphenyl phosphine to provide the compound of formula

   X' wherein Δ and the dotted lines are as previously described.

Step H and I

In Step H of reaction Scheme III, a compound of formula VI' is treated with a compound of formula X in the presence of a strong base (such as the lower alkyl or aryllithium reagents previously referred to) to produce the compound of formula XI, utilizing a Wittig reaction. Any of the conditions conventional in condensing an aldehyde and a phosphonium salt, which permits formation of a cis carbon-carbon double bond, may be employed. Generally this reaction is initiated at low temperatures such as at a temperature of about −40° under an inert atmospheric pressure, and then brought to room temperature for conventional extraction of product after the reaction between the compound of formula VI' and formula X has been completed.

The compound of formula XI may be converted to the corresponding acid, a compound of formula XII, by any conventional saponification or hydrolysis or dealkylation reaction. For example saponification or hydrolysis may be effected by treating a compound of formula XI with an alkaline metal hydroxide such as NaOH, KOH, LiOH or the like at room temperature. While, for example, dealkylation may be effected by treating a compound of formula XI with an alkaline metal halide such as LiI, KI, CsI or the like in a pyridine solvent. Suitable pyridine solvents include pyridine and methylated pyridines such as collidine, lutidine and the like. It is preferred that dealkylation be carried out using lithium iodide in a pyridine solvent.

More particularly for example a compound of formula VI' such as the compound of formula VI" may be condensed with a compound of formula X such as the compound of formula X' to provide the compound of formula

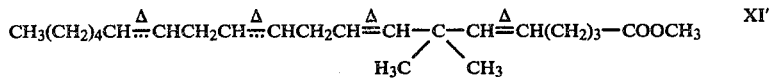   XI' wherein Δ and the dotted lines are as previously defined.

The compound of formula XI' then can be converted by conventional hydrolysis to a compound of formula

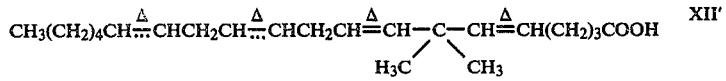   XII' wherein Δ and the dotted lines are as previously defined.

The novel compounds of formula XII are potent inhibitors of SRS-A biosynthesis and therefore are useful as anti-allergic agents or anti-asthmatic agents; while compounds of formula IV, VI, and X are useful as intermediates in producing compounds of formula XII as by processes described above.

Prophylactically effective amounts of a compound of formula XII, salts or esters thereof or pharmaceutical compositions containing prophylactically effective amounts of these compounds can be administered by methods well known in the art. Thus they can be administered, either singly or with other pharmaceutical agents, e.g., antagonists of mediators of anaphylaxis such as antihistamines, or anti-asthmatic steroids such as prednisone and prednisolone, orally, parenterally or by inhalation, e.g., in the form of an aerosol, micropulverized powder or nebulized solution. For oral administration they can be administered in the form of pills, tablets, capsules, e.g., in admixture with talc, starch, milk sugar or other inert ingredients, i.e. pharmaceutically acceptable carriers, or in the form of aqueous solutions, suspensions, encapsulated suspensions, gels, elixirs or aqueous alcoholic solutions, e.g., in admixture with sugar or other sweetening agents, flavorings, colorants, thickeners and other conventional pharmaceutical excipients. For parenteral administration, they can be administered in solutions or suspension, e.g., as an aqueous or peanut oil solution or suspension using excipients and carriers conventional for this mode of administration. For administration as aerosols, they can be dissolved in a suitable pharmaceutically acceptable solvent, e.g., ethyl alcohol or water or combinations of miscible solvents, and mixed with a pharmaceutically acceptable propellant. Such aerosol compositions are packaged for use in a pressurized container fitted with an aerosol valve suitable for release of the pressurized composition. Preferably, the aerosol valve is a metered valve, i.e., one, which on activation, releases a predetermined effective dose of the aerosol composition.

In practicing the method of the invention, the dose of compound of formula XII or salts or esters thereof to be administered and the frequency of administration will be dependent on the potency and duration of activity of the particular compound to be administered and on the route of administration, as well as the severity of the condition, age of the mammal to be treated, etc. Doses of compound of formula XII contemplated for use in practicing the method of the invention are about 0.01 to be 100 mg per kilogram of body weight per day, preferably about 0.1 to about 10 mg per kilogram of body weight per day, either as a single dose or in divided doses.

The following examples are further illustrative of the invention but are not meant to restrict the invention in scope or spirit.

EXAMPLE I

To a suspension of 4.43 g (10 mmols) of (4-carboxybutyl)triphenylphosphonium bromide in 20 ml of hexamethylphosphorictriamide and 28 ml of tetrahydrofuran was added dropwise at 0°-5° C., and under argon, 12 ml of 1.6 M butyllithium in hexane. The reaction mixture turned deep red in color. After stirring for 1 hr. at room temperature, 1.08 g (5.86 mmoles) of 2,2-dimethyl-3-[(tetrahydro-2H-pyran-2-yl)oxy]propanal (H. Marschall, et al., Chem. Ber. 107, 887 (1974)) in 3 ml of tetrahydrofuran was added. The resulting mixture was stirred for 17 hrs. at room temperature and then diluted with brine and extracted with hexane. The aqueous phase was acidified with a saturated solution of oxalic acid and extracted four times with ether. The ether extracts were combined, dried over anhydrous magnesium sulfate, filtered, and the solvent was removed in vacuo to yield 2.4 g of crude (Z)-7,7-dimethyl-8-[(tetrahydro-2H-pyran-2-yl)oxy]-5-octenoic acid which was subsequently converted into the methyl ester derivative by treatment with a freshly prepared ethereal solution of diazomethane. The crude ester (2.35 g), obtained after removal of the solvent, was chromatographed on a silica gel column. A mixture of hexane-ether (7:3) eluted 1.24 g (75.2%) of (Z)-7,7-dimethyl-8-[(tetrahydro-2H-pyran-2-yl)oxy]-5-octenoic acid methyl ester. This material was dissolved in 15 ml of methanol and treated with 0.5 ml of 2 N hydrochloric acid. The mixture was stirred for 3 hrs. at room temperature. Ca. 10 ml of methanol was evaporated in vacuo. The remaining solution was diluted with ether and poured into a saturated solution of sodium bicarbonate. The organic layer was washed with brine, dried ($MgSO_4$), and concentrated under reduced pressure to yield 0.940 g of crude material. Chromatographic purification of the product on a silica gel column yielded 0.610 g (69.8%) of pure (Z)-8-Hydroxy-7,7-dimethyl-5-octenoic acid methyl ester (98.9% pure, by GC).

Anal. Calcd. for $C_{11}H_{20}O_3$: C, 65.97; H, 10.07. Found: C, 66.03; H, 9.85.

EXAMPLE II 0.530 g (2.65 mmoles) of (Z)-8-Hydroxy-7,7-dimethyl-5-octenoic acid methyl ester in 5 ml of methylene chloride was added slowly to a mixture of $CrO_3$ (2.1 g; 21 mmol) and pyridine (3.5 g; 42 mmol) suspended in 55 ml of methylene chloride at room temperature. The reaction mixture was stirred for 5 hrs. The dichloromethane phase was decanted, and the precipitate was washed three times with ether. The organic phases were combined, washed with chilled 1 N sodium hydroxide, 1 N sulfuric acid, saturated sodium bicarbonate solution and brine then dried ($MgSO_4$) and concentrated to give 0.53 g of crude material. Purification by chromatography or a silica gel column afforded 0.405 g (77.1%) of pure (Z)-8-Oxo-7,7-dimethyl-5-octenoic acid methyl ester (100% pure, by GC-analysis).

Anal. Calcd. for $C_{11}H_{18}O_3$: C, 66.64; H, 9.15. Found: C, 66.94; H, 9.14.

EXAMPLE III

To a solution of 8.7 g (45 mmoles) of p-toluenesulfonyl chloride in 60 ml pyridine was added dropwise at 0°-5° C., a solution of 5.8 g (31.8 mmoles) of (Z,Z)-3,6-dodecadienol (T. Kajiwara, J. Sekiya, Y. Odake and A. Hatanaka, Agric. Biol. Chem., 41, 1481 (1977)). The temperature was allowed to rise to 25° C., and the reaction mixture was stirred at room temperature overnight. The resulting suspension was slowly poured into a mixture of 1 N aqueous sulfuric acid and ice and the product extracted with ether. The ether extracts were combined, washed with 10% sodium chloride solution, dried over anhydrous magnesium sulfate, and the solvent evaporated under reduced pressure. The residue (8.0 g) was chromatographed on a silica gel column. Elution with 1:1 hexane-ether gave 4.9 g (14.6 mmoles) (45.8%) of (Z,Z)-3,6-dodecadienyl tosylate, which was dissolved in 20 ml of acetone.

This solution was added at 0°-5° C. to a solution of 9.8 g (65 mmoles) of NaI in 90 ml of acetone. After stirring at room temperature for 17 hrs., most of the acetone (ca. 70 ml) was removed in vacuo. The residue was diluted with hexane and poured into 10% sodium bisulfite solution. The hexane solution was washed twice with water, dried ($MgSO_4$), and evaporated under reduced pressure. The residue (4.19 g) was evaporatively distilled to give 4.1 g (96.2%) of (Z,Z)-1-iodo-3,6-dodecadiene. (90.2% pure by GC).

Anal. Calcd. for $C_{12}H_{21}I$: C, 49.33; H, 7.24 Found: C, 49.00; H, 7.23.

EXAMPLE IV

A mixture of (Z,Z)-1-iodo-3,6-dodecadiene (1.02 g; 3.49 mmoles) and triphenylphosphine (0.90 g; 3.41 mmoles) was heated at 90° C., under argon, for 2 hrs. The resultant glassy phosphonium salt (1.90 g) was used without purification.

EXAMPLE V

To a solution of 1.50 g (2.7 mmoles) of (Z,Z)-3,6-dodecadienyl(triphenyl)phosphonium iodide in 2.5 ml of hexamethylphosphorictriamide and 4 ml of tetrahydrofuran, under argon, was added at −40° C., 1.4 ml of a 1.6 M solution of n-butyllithium in hexane, by a syringe. Then 0.360 g (1.82 mmoles) of (Z)-8-oxo-7,7-dimethyl-5-octenoic acid methyl ester in 1 ml of tetrahydrofuran was immediately added to the reaction mixture. The resulting mixture was stirred for 20 min. at −40° C., then the temperature was allowed to rise to room temperature. After two hours, the reaction mixture was poured into saturated ammonium chloride solution and extracted with hexane. The organic phase was washed twice with brine, dried over anhydrous magnesium sulfate, and the solvent was removed in vacuo. The crude material so obtained (0.93 g) was chromatographed on a silica gel column. Hexane-ether (1:1) eluted 0.604 g (95%) of (all Z)-7,7-dimethyleicosa- 5,8,11,14-tetraenoic acid methyl ester (86.4% pure by GC analysis).

Anal. Calcd. for $C_{23}H_{38}O_2$: C, 79.71; H, 11.05. Found: C, 79.48; H, 10.95.

EXAMPLE VI

A mixture of (all-Z)-7,7-dimethyleicosa-5,8,11,14-tetraenoic acid methyl ester (0.130 g; 0.37 mmoles), and lithium iodide (0.420 g; 3.13 mmoles) in 3 ml of pyridine was heated at 120°–125° C. for 24 hrs. The mixture was poured into brine, acidified with 2 N HCl and extracted with ether. The ethereal extract was dried and the solvent removed in vacuo. The residue (0.105 g) was chromatographed on a silica gel column to give 98 mg (78.5%) of pure (all-Z)-7,7-dimethyleicosa-5,8,11,14-tetraenoic acid. (>99% pure by GC analysis).

Anal. Calcd. for $C_{22}H_{36}O_2$: C, 79.46; H, 10.91. Found: C, 79.02; H, 10.71.

EXAMPLE VII

To a solution of 3.20 g (17.5 mmoles) of 3-dodecyn-1-ol in 35 ml. of ethyl acetate was added 0.300 g of Lindlar catalyst (Lindlar, Helvetica Chimica Acta 35, 450 (1952)). The hydrogenation was carried out at atmospheric pressure with stirring. When the theoretical quantity of hydrogen had been taken up, the hydrogenation was stopped and the reaction mixture was filtered through Celite. After removal of the solvent, in vacuo, the residue was evaporatively distilled under reduced pressure to afford 2.95 g (91.6%) of (Z)-3-dodecen-1-ol as an oil.

EXAMPLE VIII

A 2.1 g (11.4 mmoles) sample of (Z)-3-dodecen-1-ol in 10 ml pyridine was treated with 5.7 g (30 mmoles) of p-toluenesulfonyl chloride in 30 ml of pyridine, at room temperature. After stirring for 5 hrs., the reaction mixture was diluted with ether and the product extracted. The ethereal layer was washed twice with 1 N $H_2SO_4$, water, saturated $NaHCO_3$ solution, water and dried over $MgSO_4$. The residue (3.2 g) obtained after removal of the solvent was chromatographed on silica gel. Hexane-ether 9:1 eluted 2.4 g (62.2%) of the tosylate derivative. This material (7.1 mmoles) was dissolved in 10 ml of acetone and slowly added to a solution of 4.8 g (32 mmoles) of NaI in 55 ml of acetone. After stirring for 17 hrs. at room temperature, most of the acetone was removed in vacuo. The residue was diluted with hexane. The organic layer was washed with 10% $NaHSO_3$ solution, twice with water, dried over $MgSO_4$ and concentrated under reduced pressure. Evaporative distillation of the residue produced 1.7 g (81.5%) of pure (Z)-1-iodo-3-dodecene as an oil.

EXAMPLE IX

A mixture of 0.43 g (1.46 mmoles) of (Z)-1-iodo-3-dodecene and 0.38 g (1.45 mmoles) of triphenylphosphine was heated at 90° C. for 3 hrs. under argon to produce 0.81 g of [(Z)-3-dodecen-1-yl]triphenylphosphonium iodide. This material was used without further purification.

EXAMPLE X

Using the procedure of previous examples, (all Z)-7,7-dimethyl-5,8,11-eicosatrienoic acid was prepared in 54% yield. Thus 2.05 g (3.7 mmoles) of [(Z)-3-dodecenyl]-triphenylphosphonium iodide was condensed with 0.5 g (2.5 mmoles) of (Z)-8-oxo-7,7-dimethyl-5-octenoic acid methyl ester (Wittig reaction conditions: THF/HMPT, 2:1, 2.0 ml of 1.6 M butyllithium in hexane; −78° C.) to yield 0.837 g (95%) of (all Z)-7,7-dimethyl-5,8,11-eicosatrienoic and methyl ester. Hydrolysis of this material with 0.1 ml of 5% aqueous KOH in 10 ml of methanol, followed by chromatographic purification afforded 0.535 g (65%) of (all Z)-7,7-dimethyl-5,8,11-eicosatrienoic acid as an oil.

EXAMPLE XI

Inhibition of the In Vitro Synthesis of SRS-A in Rat Peritoneal Cells

To study the effect of drugs on SRS-A synthesis in rat peritoneal cells, these cells (including mast cells, monocytes, eosinophils and neutrophils) were isolated from male Sprague-Dawley rats (Charles River Laboratories) weighing 180–220 g by the lavage procedure described by Herzig, D. G. and Dusner, E. J. Journal of Pharmacology and Experimental Therapeutics, 194, 457–460 (1975) with the exception that Hanks balanced salt solution used in these experiments was adjusted to pH 6.9 with 5% (V/V) of 0.1 M aqueous phosphate buffer and contained 50 mg/ml sodium heparin. After removal from the peritoneal cavity of rats, the cells were subsequently isolated by centrifugation at 400×gravity for 10 minutes at 4° C. and resuspended to a concentration of about 2,000,000 cells per ml in Hanks buffer.

Samples for evaluation were prepared by adding various concentrations of test drugs to 2 ml aliquots of the resuspended cells in Hanks buffer. The 2 ml samples used for control contained 2 ml aliquots of resuspended cells in Hanks buffer without drugs. All of the above samples (2 ml final volume) were preincubated at 37° C. for 10 minutes in the presence of varying concentrations of test drug prior to challenge with $5 \times 10^7$ M ionophore A23187. This ionophore is disclosed in Burka and Flower, Br. J. Pharmacology 65: 35–41 (1979). Antibiotic A23187 was used as a probe for the study of calcium and function in biological systems. After ionophore challenge, SRS-A was synthesized in the samples by the cells for 10 minutes (at 37° C.) after which this synthesis was terminated by placing the samples in a boiling water bath for 10 minutes followed by centrifugation at 2,000×g (10 minutes) at 4° C. to remove coagulated protein and cellular debris. The SRS-A present in the resulting supernatants was quantitated by a bioassay using a guinea pig ileum as described in Orange, and Austen, Adv. Immunol, 10: 105–144 (1969). For this bioassay, a 1.5 cm segment of ileum was removed from animals weighing 300 to 400 g and resuspended in an organ bath containing 10 ml of Tyrodes solution with $10^{-6}$ M atropine sulfate and $10^{-6}$ M pyrilamine maleate. The bath was maintained at 37° C. and aereated with a mixture of 95% $O_2$ and 5% $CO_2$. The concentration of SRS-A in the experimental samples was determined by a comparison of isotonic contraction responses elicited by the samples with those obtained with varying amounts of an SRS-A standard solution prepared from chopped guinea pig lung as disclosed in Hitchcock, M. J. Pharmacol. Exp. Ther. 207: 630–640 (1978) and quantitated by the procedures of Orange, R. R. and Austen, K. F. Adv. Immunol. 10: 105–144 (1969) against histamine (1 unit of SRS-A being that amount which gives a contractie response similar to that of 5 mg of histamine). In the absence of drug, the ionophore A23187-induced SRS-A synthesis varied between 40 to 50 units of SRS-A per $10^6$ cells. In the presence of increasing concentrations of test drug, there was a concentration-related decrease in SRS-A synthesis.

The mean percent inhibition $$\frac{\text{difference of units of SRS-A in test sample}}{\text{units of SRS-A in control sample}} \times 100$$

at each concentration of the various test drugs was calculated. The concentration of test drug which inhibits the synthesis of SRS-A by 50% ($IC_{50}$) was determined for each test drug from a plot of the mean percent inhibition versus drug concentration. Both the percent (%) inhibition at 10 μM and the $IC_{50}$ are given in the following table. The difference of units of SRS-A in the test sample used in the fraction given above was obtained by subtracting the units of SRS-A in the control from the actual measurement of the units of SRS-A in the sample.

| Test Drug | % Inhibition at 10μ M | $IC_{50}$ (μM) |
|---|---|---|
| (All Z)-7,7-Dimethyl-5,8,11,14-eicosatetraenoic acid | 100 ± 0(p<0.001) | 1-3 |
| (All Z)-7,7-Dimethyl-5,8,11-eicosatrienoic acid | 100 ± 0(p<0.001) | <10 |
| (Z,Z)-7,7-Dimethyl-5,8-eicosadienoic acid | 100 ± 0(p<0.001) | <10 |

EXAMPLE XII

A 1.4 ml. portion of n-butyllithium (1.6 M solution in hexane) was added to a solution of 1.4 g (2.74 mmol) of n-dodecyltriphenylphosphonium bromide in 5.5 ml of 2:1 tetrahydrofuran-hexamethylphosphorictriamide, at −78° C., under argon. The solution turned orange-red in color. To this solution was then added 0.350 g (1.77 mmoles) of (Z)-8-oxo-7,7-dimethyl-5-octenoic acid methyl ester dissolved in 1 ml of tetrahydrofuran, using a syringe. The reaction mixture was stirred for 30 minutes at −78° C. and an additional 45 minutes at 0° C. The product was isolated by ether extraction using the conventional workup procedure and then chromatographed on silica gel. Hexane-ether (19:1) eluted 0.600 g (97%) of (Z,Z)-7,7-dimethyl-5,8-eicosadienoic acid methyl ester. This material was dissolved in 6 ml of methanol and treated with 0.6 ml of 5% aqueous potassium hydroxide. After stirring at room temperature for 17 hours, 3 ml of the methanol was evaporated in vacuo. The remaining solution was acidified with oxalic acid and the product was extracted with ether. The ether extracts were washed with brine, dried over $MgSO_4$ and the solvent evaporated at reduced pressure. Purification of the crude acid on a silica gel column provided 0.292 g (50.7%) of (Z,Z)-7,7-dimethyl-5,8-eicosadienoic acid (ca. 100% pure by GC analysis).

EXAMPLE XIII

Capsule Formulaton of (All Z)-7,7-Dimethyl-5,8,11,14-eicostetraenoic acid

| Item | Ingredients | mg/capsule | | | | |
|---|---|---|---|---|---|---|
| 1. | (All Z)-7,7-Dimethyl 5,8,11,14-eicostetraenoic acid | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures:
1. Mix Items 1-3 in a suitable mixer. Mill through a suitable mill.
2. Mix with Items 4 and 5 and fill on capsule machine.

EXAMPLE XIV

Tablet Formulation (Wet Granulation) of (all Z)-7,7-Dimethyl-5,8,11,14-eicosatetraenoic acid

| Item | Ingredients | mg/capsule | | | | |
|---|---|---|---|---|---|---|
| 1. | (All Z)-7,7-Dimethyl-5,8,11,14-eicosatetraenoic acid | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure:
1. Mix Items 1-5 in a suitable mixer, granulate with water. Dry, mill.
2. Mix with Item 5 and compress on a suitable press.

EXAMPLE XV

Tablet Formulation (Direct Compression) of (All Z)-7,7-Dimethyl-5,8,11,14-eicosatetraenoic acid

| Item | Ingredients | mg/capsule | | | | |
|---|---|---|---|---|---|---|
| 1. | (All Z)-7,7-Dimethyl-5,8,11,14-eicosatetraenoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure:
1. Mix Items 1-5 in a suitable mixer for 10-15 minutes.
2. Add magnesium stearate (Item 5) as a premix and mix for 4 miuntes.
3. Compress on a suitable press.

EXAMPLE XVI

Capsule Formulations of (All Z)-7,7-Dimethyl-5,8,11-eicosatrienoic acid

| Item | Ingredients | mg/capsule | | | | |
|---|---|---|---|---|---|---|
| 1. | (All Z)-7,7-Dimethyl-5,8,11-eicosatrienoic acid | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium | 1.0 | 1.0 | 1.0 | 2.0 | 3.0 |

EXAMPLE XVII

Tablet Formulation (Direct Compression) of (All Z)-7,7-Dimethyl-5,8,11-eicosatrienoic acid

| Item | Ingredients | mg/tablet | | | | |
|---|---|---|---|---|---|---|
| 1 | (All Z)-7,7-Dimethyl-5,8,11-eicosatrienoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedures:
1. Mix Items 1-5 in a suitable mixer for 10-15 minutes.
2. Add magnesium stearate (Item 5) as a premix and mix for 4 minutes.
3. Compress on a suitable press.

EXAMPLE XVIII

Tablet Formulation (Wet Granulation of (All Z)-7,7-Dimethyl-5,8,11-eicosatrienoic acid methyl ester

| Item | Ingredients | mg/tablet | | | | |
|---|---|---|---|---|---|---|
| 1. | (All Z)-7,7-Dimethyl-5,8,11-eicosatrienoic acid | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure:
1. Mix Items 1-5 in a suitable mixer, granulate with water. Dry, mill.
2. Mix with Item 5 and compress on a suitable press.

EXAMPLE XIX

Capsule Formulation of (Z,Z)-7,7-Dimethyl-5,8-eicosadienoic acid oxazole

| Item | Ingredients | mg/capsule | | | | |
|---|---|---|---|---|---|---|
| 1. | (Z,Z)-7,7-Dimethyl-5,8-eicosadienoic acid | 0.1 | 0.5 | 5.0 | 10.0 | 25.0 |
| 2. | Lactose | 183.5 | 183.9 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedure:
1. Mix Items 1-3 in a suitable mixer. Mill through a suitable mill.
2. Mix with Items 4 and 5 and fill on capsule machine.

EXAMPLE XX

Tablet Formulation (Direct Compression) of (Z,Z)-7,7-Dimethyl-5,8-eicosadienoic acid

| Item | Ingredients | mg/tablet | | | | |
|---|---|---|---|---|---|---|
| 1. | (2,2)-7,7-Dimethyl-5,8-eicosadienoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure:
1. Mix Items 1-5 in a suitable mixer for 10-15 minutes.
2. Add magnesium stearate (Item 5) as a premix and mix for 4 minutes.
3. Compress on a suitable press

EXAMPLE XXI

Tablet Formulation (Wet Granulation) of (Z,Z)-7,7-Dimethyl-5,8-eicosadienoic acid

| Item | Ingredients | mg/tablet | | | | |
|---|---|---|---|---|---|---|
| 1. | (Z,Z)-7,7-Dimethyl-5,8-eicosadienoic acid | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 3.0 |
| Total | | 125 mg | 125 mg | 125 mg | 200 mg | 285 mg |

Procedure:
1. Mix Items 1-5 in a suitable mixer, granulate with water. Dry, mill.
2. Mix with Item 5 and compress on a suitable press.

EXAMPLE XXII

Capsule Formulation (All Z)-7-methyleicosa-5,8,11,14-tetraenoic acid

| Item | Ingredients | mg/capsule | | | | |
|---|---|---|---|---|---|---|
| 1. | (All Z)-7-methyleicosa-5,8,11,14-tetraenoic acid | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| Total | | 220 mg | 220 mg | 220 mg | 290 mg | 370 mg |

Procedures:
1. Mix Items 1-3 in a suitable mixer. Mill through a suitable mill.
2. Mix with Items 4 and 5 and fill on capsule machine.

EXAMPLE XXIII

Tablet Formulation (Wet Granulation) of (All Z)-7-methyleicosa-5,8,11,14-tetraenoic acid

| Item | Ingredients | mg/capsule | | | | |
|---|---|---|---|---|---|---|
| 1. | (All Z)-7-methyleicosa-5,8,11,14-tetraenoic acid | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregaltinized Starch | 10.0 | 10.0 | 10.0 | 20.0 | 30.0 |
| 5. | Magnesium Stearate | 1.0 | 1.0 | 1.0 | 2.0 | 3.0 |
| | Total | 125 mg | 125 mg | 125 mg | 200 mg | 285 mg |

Procedure:
1. Mix Items 1-5 in a suitable mixer, granulate with water. Dry, mill.
2. Mix with Item 5 and compress on a suitable press.

EXAMPLE XXIV

Tablet Formulation (Direct Compression) of (All Z)-7-methyleicosa-5,8,11,14 tetraenoic acid

| Item | Ingredients | mg/capsule | | | | |
|---|---|---|---|---|---|---|
| 1. | (All Z)-7-methyleicosa 5,8,11,14 tetraenoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure:
1. Mix Items 1-5 in a suitable mixer for 10-15 minutes.
2. Add magnesium stearate (Item 5) as a premix and mix for 4 minutes.
3. Compress on a suitable press.

EXAMPLE XXV

Capsule Formulations of (All Z)-7-methyleicosa-5,8,11-trienoic acid

| Item | Ingredients | mg/tablet | | | | |
|---|---|---|---|---|---|---|
| 1. | (All Z)-7-methyleicosa-5,8,11-trienoic acid | 0.1 | 0.5 | 5.0 | 10.0 | 25.0 |
| 2. | Lactose | 183.9 | 183.5 | 179.0 | 281.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures:
1. Mix Items 1-3 in a suitable mixer. Mill through a suitable mill.
2. Mix with Items 4 and 5 and fill on capsule machine

EXAMPLE XXVI

Tablet Formulation (Direct Compression) of (All Z)-7-methyleicosa-5,8,11-trienoic acid

| Item | Ingredients | mg/tablet | | | | |
|---|---|---|---|---|---|---|
| 1. | (All Z)-7-5,8,11-trienoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.5 |
| | Total | 125 mg | 125 mg | 125 mg | 170 mg | 215 mg |

Procedure:
1. Mix Items 1-5 in a suitable mixer for 10-15 minutes.
2. Add magnesium stearate (Item 5) as a premix and mix for 4 minutes.
3. Compress on a suitable press.

EXAMPLE XXVII

Tablet Formulation (Wet Granulation) of (All Z)-7-methyleicosa-5,8,11-trienoic acid

| Item | Ingredients | mg/tablet | | | | |
|---|---|---|---|---|---|---|
| 1. | (All Z)-7-methyleicosa-5,8,11-trienoic acid | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0 | 2.0 |
| | Total | 125 mg | 125 mg | 125 mg | 200 mg | 285 mg |

Procedure:
1. Mix Items 1-5 in a suitable mixer, granulate with water. Dry mill.
2. Mix with Item 5 and compress on a suitable press.

EXAMPLE XXVIII

Capsule Formulation of (Z,Z)-7-methyleicosa-5,8-dienoic acid

| Item | Ingredients | mg/capsule | | | | |
|---|---|---|---|---|---|---|
| 1. | (Z,Z)-7-methyleicosa-5,8-dienoic acid | 0.1 | 0.5 | 5.0 | 10.0 | 25.0 |
| 2. | Lactose | 183.9 | 183.5 | 179.0 | 218.0 | 257.0 |
| 3. | Starch | 30.0 | 30.0 | 30.0 | 50.0 | 70.0 |
| 4. | Talc | 5.0 | 5.0 | 5.0 | 10.0 | 15.0 |
| 5. | Magnesium Stearate | 1.0 | 1.0 | 1.0 | 2.0 | 3.0 |
| | Total | 220 mg | 220 mg | 220 mg | 290 mg | 370 mg |

Procedures:
1. Mix Items 1-3 in a suitable mixer. Mill through a suitable mill.
2. Mix with Items 4 and 5 and fill on capsule machine.

EXAMPLE XXIX

Tablet Formulation (Direct Compression) of (Z,Z)-7-methyleicosa-5,8-dienoic acid

| Item | Ingredients | mg/tablet | | | | |
|---|---|---|---|---|---|---|
| 1. | (Z,Z)-methyleicosa-5,8-dienoic acid | 0.1 | 0.5 | 5.0 | 10.0 | 25.0 |
| 2. | Lactose | 85.4 | 85.5 | 81.0 | 103.0 | 112.5 |
| 3. | Avicel | 30.0 | 30.0 | 30.0 | 45.0 | 60.0 |
| 4. | Modified Starch | 8.0 | 7.5 | 7.5 | 10.0 | 15.0 |
| 5. | Magnesium Stearate | 1.5 | 1.5 | 1.5 | 2.0 | 2.0 |
| | Total | 125 mg | 125 mg | 125 mg | 170 mg | 215 mg |

Procedure:
1. Mix Items 1-5 in a suitable mixer for 10-15 minutes.
2. Add magnesium stearate (Item 5) as a premix and mix for 4 minutes.
3. Compress on a suitable press.

EXAMPLE XXX

Tablet Formulation (Wet Granulation) of (Z,Z)-7-methyleicosa-5,8-dienoic acid

| Item | Ingredients | mg/tablet | | | | |
|---|---|---|---|---|---|---|
| 1. | (Z,Z)-7-methyleicosa-5,8-dienoic acid | 0.1 | 0.5 | 5.0 | 10.0 | 25.0 |
| 2. | Lactose | 103.9 | 103.5 | 99.0 | 148.0 | 197.0 |
| 3. | Modified Starch | 10.0 | 10.0 | 10.0 | 20.0 | 30.0 |
| 4. | Pregelatinized Starch | 10.0 | 10.0 | 10.0 | 20.0 | 30.0 |
| 5. | Magnesium Stearate | 1.0 | 1.0 | 1.0 | 2.0/ | 3.0 |
| | Total | 125 mg | 125 mg | 125 mg | 200 mg | 285 mg |

Procedure:
1. Mix Items 1–5 in a suitable mixer, granulate with water. Dry, mill.
2. Mix with Item 5 and compress on a suitable press.

What is claimed is:

1. A compound of the formula:

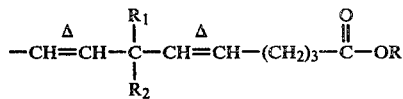

wherein $\Delta$ designates a cis configuration, R is hydrogen or lower alkyl; and $R_1$ and $R_2$ are hydrogen or methyl with the proviso that where one of $R_1$ and $R_2$ is hydrogen the other is methyl, and pharmaceutically acceptable salts thereof where R is hydrogen.

2. A compound according to claim 1 which is (Z,Z)-7,7-dimethyleicosa-5,8-dienoic acid.

3. A compound according to claim 1 which is (Z,Z)-7-methyleicosa-5,8-dienoic acid.

* * * * *